United States Patent [19]

Vandecasteele et al.

[11] 4,221,869

[45] Sep. 9, 1980

[54] ENZYMATIC SYNTHESIS OF L-CARNITINE

[75] Inventors: Jean-Paul Vandecasteele, Fourqueux; Jeannine Lemal, Rueil Malmaison, both of France

[73] Assignee: Institut Francais Du Petrole, Rueil-Malmaison, France

[21] Appl. No.: 925,356

[22] Filed: Jul. 17, 1978

[30] Foreign Application Priority Data

Jul. 18, 1977 [FR] France .................. 77 22183

[51] Int. Cl.² .......................................... C12P 17/00
[52] U.S. Cl. .................... 435/117; 435/874; 435/875; 435/876; 435/877
[58] Field of Search ............... 195/29, 30; 435/117

[56] References Cited

PUBLICATIONS

The Merck Index, 9th Ed., p. 236; 1976.

*Primary Examiner*—Robert J. Warden
*Attorney, Agent, or Firm*—Millen & White

[57] ABSTRACT

L-carnitine is obtained by reacting 3-dehydrocarnitine or one of its salts, in aqueous medium, simultaneously with:
(a) carnitine dehydrogenase,
(b) a coenzyme utilized by carnitine dehydrogenase for reducing dehydrocarnitine, preferably nicotinamide adenine dinucleotide, and
(c) a reducing agent for the coenzyme, the coenzyme (b) and carnitine dehydrogenase being preferably used in catalytic amount.

23 Claims, No Drawings

ENZYMATIC SYNTHESIS OF L-CARNITINE

Chemical syntheses of carnitine have been disclosed but they yield the racemic mixture and not L-carnitine which is the desired product for biologic activity.

The present invention discloses a process for manufacturing L-carnitine by asymmetrical reduction of 3-dehydrocarnitine whose chemical synthesis has been disclosed, for example, by Aurich et al., Hoppe-Seyler's Z. Physiol. Chem. 349 (1968), 1310. The process consists of reacting 3-dehydrocarnitine or one of its salts with the following elements used simultaneously in aqueous medium:

(a) Carnitine dehydrogenase,
(b) A coenzyme which may be utilized by carnitine dehydrogenase for reducing dehydrocarnitine, such as nicotinamide adenine dinucleotide. Only the latter compound will be referred to in the following disclosure, since its use represents a preferred embodiment of the invention.
(c) A chemical or enzymatic system or agent for reducing the oxidized form of nicotinamide adenine dinucleotide. This system comprises in each case a reducer (R) and further, in case of a system for enzymatic reduction, an enzyme (E).

The elements (a) and (b) and the enzyme (E), when used in (c) are preferably used in catalytic amount whereas, reducer (R), used in (c), is a reactant and must be present in a substantial amount, preferably at least the stoichiometic proportion with respect to 3-dehydrocarnitine.

The reaction may be interpreted as follows: carnitine dehydrogenase referred to in the International Enzyme Nomenclature (published in 1972 by Elsevier, Amsterdam) as E.C. 1.1.1.108 is a catalyst for the reaction:

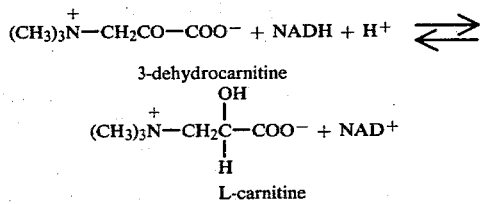

Nicotinamide adenine dinucleotide in the reduced form (NADH) is oxidized to nicotinamide adenine dinucleotide (NAD+) in this reaction. It is converted back to NADH in a second reaction, by means of a reducer R which is oxidized to a product P. This second reaction is, in certain cases, catalyzed by an enzyme E. It may be written as:

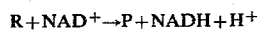

The aggregate scheme of L-carnitine sysnthesis is:

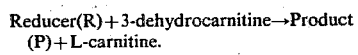

The advantage of such a system is obvious since nicotinamide adenine dinucleotide, an expensive material (either in the reduced or the oxidized form), may be used in catalytic amount only.

L-carnitine may be synthesized in a reactor maintained at a temperature of from 10° to 60° C., preferably from 20° to 45° C. The pH is maintained at a value of from 5.5 to 10, for example by means of an automatic control device. A pH of from 6.5 to 8.5 is particularly favourable to the stability of the enzymes employed and to nicotinamide adenine dinucleotide. The pH selection is important for the latter compound whose reduced form (NADH) is unstable in acidic medium and whose oxidized form (NAD+) is unstable in basic medium. A buffer, for example a soluble salt of phosphoric acid, such as an ammonium, sodium or potassium phosphate, may be useful in certain cases for maintaining the pH of the medium and thus the stability of the enzymes.

The elements necessary to the considered synthesis, i.e. NAD+ (or NADH), carnitine dehydrogenase, the reducer R (and if necessary the enzyme E for oxidation thereof) are introduced into the reactor, which may also contain a buffer and stabilization agents for the enzymes. Among the latter the thiol compounds, such as 2-mercaptoethanol, dithiothreitol, etc., are particularly efficient. As a rule, however, the presence of a substantial concentration of 3-dehydrocarnitine in the reactor should be avoided since it has been found that this material decarboxylates very quickly at all pHs except at highly acidic pHs (lower than 2). For this reason, it is preferred to introduce this compound continuously into the reactor as a highly acidic solution. In that case the injection rate is so regulated that the limiting reaction factor is the dehydrocarnitine supply, the latter compound being immediately converted to L-carnitine as it is introduced into the reactor. Dehydrocaronitine supply is considered as limiting when any modification (increase or decrease) of this supply results in a parallel modification of the L-carnitine production rate.

When a sufficient amount of L-carnitine has been produced, the latter may be extracted from the liquid medium, for example, by passage on an ion exchange resin. After elution, it may be obtained in the solid state by evaporation in vacuo.

The enzymes and nicotinamide adenine dinucleotide, which are catalysts for this synthesis, may be used again and their cost may justify in certain cases their recovery at the end of the reaction. The recovery of the enzymes is particularly easy (for example by decantation or filtration) when they are used immobilized on a solid carrier. These enzymes may be used in the purified or unpurified form; microorganisms containing the necessary enzymes may also be used directly in appropriate conditions. As concerns nicotinamide adenine dinucleotide, its recovery for further use may be effected, for example, by passage through a column filled with an adsorbent, such as charcoal.

When using nicotinamide adenine dinucleotide as soluble derivative of high molecular weight or attached to a solid carrier, its recovery is possible by dialysis in the first case or by direct decantation in the second case.

The coenzymes to be used by carnitine dehydrogenase for reducing dehydrocarnitine are nicotinamide adenine dinucleotide or its equivalents which are usually compounds whose structure is of the pyridine purine dinucleotide type, for example nicotinamide hypoxanthine dinucleotide or acetylpyridine adenine dinucleotide. These coenzymes may be attached to a soluble derivative of high molecular weight or to a solid carrier as hereinbefore indicated. Nicotinamide adenine dinucleotide is preferred in view of the high activity obtained when reducing dehydrocarnitine.

The enzymes necessary to the performed synthesis are usually obtained by culture of a producing microorganism in appropriate conditions. Some of them are available in the trade. As concerns carnitine dehydrogenase it has been found that bacteria of the Pseudomonas genus, particularly Pseudomonas of the fluorescent group such as defined by Stainer et al. (J. Gen. Microbiol. 43, 159-271, 1966) may be used to produce this enzyme in a quite effective manner. Examples thereof are *Pseudomonas aeruginosa*, *Pseudomonas putida* (or *Pseudomonas ovalis*), for example *P. putida* $T_1$ and *P. putida* 572 from the collection of Institut Francais du Pétrole, *P. putida* CIP 52191 (CIP being for collection of Institut Pasteur), *Pseudomonas fluorescens*, for example *P. fluoroescens* CIP 7325 or *P. fluorescens* CIP 6913.

The system for NAD+ reduction (also called system for NADH regeneration) may be of the chemical type. It then consists of the reducer R which may be, for example, an alkali metal dithionite or hydrogen in the presence of an active catalyst, for example, a noble metal of group VIII, such as platinum. When the system for NADH regeneration is of the enzymatic type, the reducers (R) are diverse and consist of compounds whose oxidation is catalyzed by a dehydrogenase able to utilize NAD+, i.e. an enzyme of the 1.1.1. class of the above mentioned International Enzyme Classification. This constitutes the enzyme (E), specific for reducer (R), which is then named a substrate of the enzyme (E). The system for NADH regeneration is preferably so selected that reducer R is an inexpensive material and the enzyme E is easily obtained, particularly by culture of an appropriate microorganism.

Alcohol dehydrogenase (E.C. 1.1.1.1) may, for example, be used with ethanol as substrate (the catalyzed reaction is: ethanol+NAD+$\rightleftarrows$acetaldehyde+-NADH+H+). The enzyme may be obtained in large amount from baker yeast (Saccharomyces cerevisiae). Another example is glucose dehydrogenase (E.C. 1.1.1.47); the catalyzed reaction is: glucose+NAD+$\rightleftarrows$-gluconolactone+NADH+H+; the enzyme may be obtained by culture of bacteria of the Bacillus genus, particularly *Bacillus subtilis*, *Bacillus cereus*, *Bacillus megaterium*. The latter system is particularly advantageous since glucose dehydrogenase has good stability in the conditions of use and the carnitine yields are very high as shown by the following examples. It is thought that these high yields result at least partly from the fact that the glucose oxidation reaction is strongly favoured since the resulting product, gluconolactone, spontaneously hydrolyses to gluconic acid, thus strongly improving the NADH formation. Other reactions where the NADH formation is favoured have another advantage. This is the case for the reactions catalyzed by hydrogenases, particularly the NAD+ hydrogenases (hydrogen: NAD+ oxidoreductases E.C. 1.12.1.2) which may be obtained from bacteria consuming aerobic molecular hydrogen, for example *Alcaligenes eutrophus* (*Hydrogenomonas eutropha*), *Pseudomonas saccharophila*, *Pseudomonas ruhlandii*, *Nocardia opaca*. The reaction catalyzed by this enzyme $$H_2 + NAD^+ \rightleftarrows NADH + H^+$$

has the advantage of avoiding the problem of separating synthesized L-carnitine from any product or reactant of the reaction of NADH formation. Similar advantages (reaction favouring the NADH formation, absence of products to be separated) are obtained when using formate dehydrogenase (E.C. 1.2.1.2) which catalyzes the reaction:

$$HCOO^- + NAD^+ \rightarrow CO_2 + NADH.$$

The source of the HCOO− ion may be a soluble salt of formic acid, for example a sodium, potassium or ammonium salt. Formate dehydrogenase may be obtained, for example, by cultivating strict methylotrophic microorganisms (assimilating only methane, methanol or methylamine), such as bacteria of the Methylosinus, Methylocystis, Methylococcus, Methylomonas, Methylobacter groups, or optional methylotrophic microorganisms (assimilating both the compounds with one carbon atom and the other carbon sources). Among the latter, there can be used yeasts of the Candida, Kloeckera, Pichia, Hansenula or Torulopsis genus or bacteria of the Pseudomonas, Xanthomonas or Flavobacterium genus.

The following non-limitative examples illustrate the invention. In the following, M and mM are intended to designate the concentration of a solution expressed in moles or millimoles of solute per liter of solution.

EXAMPLE 1

Production of carnitine dehydrogenase

A strain of *Pseudomonas putida* (CIP 52191) was cultivated in two 1-liter Fernbach bottles each containing 200 ml of inorganic medium comprising, per liter of distilled water:

| | |
|---|---|
| $KH_2PO_4$ | 4 g |
| $Na_2HPO_4$, 12 $H_2O$ | 6 g |
| $MgSO_4$, 7 $H_2O$ | 0.3 g |
| $FeSO_4$, 7 $H_2O$ | 1 mg |
| $ZnSO_4$, 7 $H_2O$ | 0.1 mg |
| $CuSO_4$, 5 $H_2O$ | 0.1 mg |
| $MnSO_4$, 7 $H_2O$ | 0.04 mg |

20 g/liter of DL-carnitine hydrochloride was added to this inorganic medium as the only source of carbon and nitrogen (necessary for inducing the bacterial synthesis of carnitine dehydrogenase). The pH was adjusted to 7.0 with potassium hydroxide. After sterilization at 115° C. for 20 minutes in an autoclave, it was seeded with 10 ml of a culture made in the same conditions from a sample of the strain on gelose. The culture was effected at 30° C. for 24 hours with stirring (alternative motion of 80 periods per minute). The cells were collected at 4° C. by centrifugation; 3.6 g of cells (wet weight) for 400 ml medium was obtained.

The cells were suspended in a potassium phosphate buffer (100 ml) at pH 7.0 (3.6 g of cells in 6 ml buffer) and broken by ultra-sonic treatment at a temperature between 0° and 10° C. The lighter phase obtained by centrifugation constituted the enzymatic extract to be used. This extract contained 95 mg/ml of proteins and had a carnitine dehydrogenase activity of 0.55 unit per mg of proteins. The international enzymatic unit was employed for all enzymes of the present invention. It is defined as the activity ensuring the conversion of 1 micromole substrate per minute, the conditions being a saturating concentration of the substrate, the pH of maximum activity and a temperature of 30° C.

SYNTHESIS OF L-CARNITINE

L-carnitine was synthesized in a reactor containing 51 ml of medium comprising the following constituents at the concentrations given in millimoles per liter (mM): 100 mM ammonium phosphate (pH=6.8), 1 mM NAD+, 0.2 mM dithiothreitol and 200 mM glucose. 0.5 ml (75 units) glucose dehydrogenase (purified Boehringer enzyme, ref. 171697) and 0.5 ml (26 units) of the carnitine dehydrogenase extract were added. An 0.4 M aqueous solution of dehydrocarnitine hydrochloride (brought to pH 0.5 by hydrochloric acid addition) was then injected at a rate of 0.5 ml per hour. The reactor was maintained at 25° C. and the pH at 6.8 by addition of 1 N solution of ammonia controlled with a pH-meter regulator. After 40 h and 30 minutes the reaction was discontinued. L-carnitine was titrated enzymatically by means of carnitine acetyltransferase. A concentration of 80 mM of L-carnitine in a volume of 95.5 ml was measured, which corresponds to a production of 1.5 g carnitine (expressed as the hydrochloride both here and in the following disclosure) with a 94% yield with respect to dehydrocarnitine hydrochloride.

PURIFICATION OF L-CARNITINE

The reaction product was passed through a column of cation exchange resin Dowex AG 50W-X8 of 20×200 mm. This column had been previously brought to the H+ form by washing with 350 ml of 10% HCl and then with 500 ml of water. After introduction of the sample, the column was washed with 400 ml of water and then eluted with a 1-normal ammonia solution. The fraction discharged from the column between 150 ml and 225 ml, after the beginning of the elution with ammonia, was collected. By carnitine acetyltransferase titration, it was found to contain 1.48 g of carnitine. The sample was then evaporated in vacuo, re-dissolved into water (15 ml) and evaporated again. The carnitine base was converted to the hydrochloride by addition of 8 ml of a 1-normal HCl solution and evaporated again. The deliquescent product was dissolved into 75 ml of an anhydrous mixture of 3 parts of acetone with 2 parts of ethanol. 210 ml of acetone at 0° C. was added and the solution was stored at −9° C. for 12 hours. The crystals were collected, washed with ether and dried under vacuum. 0.91 g of carnitine was obtained. The final product was titrated with carnitine acetyltransferase and found to contain 89.5% of L-carnitine hydrochloride. It was obtained with an aggregate yield of 57% with respect to dehydrocarnitine hydrochloride.

EXAMPLE 2

Carnitine dehydrogenase obtained as in example 1 was used in that synthesis. Synthesis of L-carnitine was carried out in the same conditions as in example 1, except as concerns the NADH regeneration system which was the yeast alcohol dehydrogenase and ethanol system instead of the glucose dehydrogenase and glucose system. Glucose was thus substituted with ethanol (concentration in the reactor: 4% by volume) and glucose dehydrogenase with 4 mg (700 units) of purified yeast alcohol dehydrogenase (Sigma ref. A 3263). Nitrogen was bubbled through the reactor (80 ml/mn) to eliminate the acetaldehyde formed by alcohol oxidation and thus improve the NADH regeneration. After 30 h, 0.325 g of L-carnitine was produced from dehydrocarnitine hydrochloride with a yield of 27%.

EXAMPLE 3

Carnitine was synthesized as in example 2, except that the NADH regeneration system comprised, in addition to alcohol dehydrogenase, aldehyde dehydrogenase (E.C. 1.2.1.5) which oxidizes the aldehyde (formed by action of alcohol dehydrogenase on ethanol) to acetic acid. Two molecules of NADH were formed from one molecule of ethanol (instead of one in the preceeding example) and the reaction balance was strongly displaced in favour of NADH and acetic acid formation. It was thus no longer necessary to eliminate acetaldehyde as in the preceeding example. The conditions were thus those of example 2, except that 125 units of purified aldehyde dehydrogenase (Boehringer ref. 171.832) were added to the reaction medium and nitrogen bubbling was omitted. After 24 hours, 0.764 g of L-carnitine was formed with a yield of 77.5% with respect to dehydrocarnitine hydrochloride.

EXAMPLE 4

Carnitine was synthesized as in example 2, except that yeast alcohol dehydrogenase, instead of being used as the purified free enzyme, was used in the unpurified and undissolved form. In fact cells of baker yeast (of high alcohol dehydrogenase content) were used after a treatment of permeabilization and immobilization in a polyacrylamide gel. The permeabilization treatment was effected as follows: 18 g of baker yeast cells were suspended in 36 ml of 40 mM potassium phosphate buffer at pH 8. After centrifugation and decantation, the cells were taken up again in 36 ml of the same buffer. 1.8 ml of a 1:4 (by volume) mixture of toluene and ethanol was added and incubation was effected at 30° C. for 30 minutes. It was then centrifuged and washed two times with 36 ml of buffer. The cells thus made permeable were immobilized in a gel prepared by suspending the cells in 4 ml of phosphate buffer (40 mM) at pH 8 and adding 500 mg of acrylamide, 40 mg of N,N' methylene bis acrylamide, 0.5 ml of N,N,N',N'-tetramethylethylethylene diamine at 0.805% concentration and 0.5 ml of ammonium persulfate at 2.5% concentration. The solution was poured into a vessel filled up with glass balls of a 2 mm diameter. The polymerization took place at 30° C. for 1 hour. The balls were removed, to leave a gel in fragments, which was washed with the same buffer.

This gel was introduced into the reactor and synthesis of carnitine was carried out. In these conditions, 0.436 g of L-carnitine was obtained in 25 hours from 1.105 g of dehydrocarnitine hydrochloride.

EXAMPLE 5

Carnitine was synthesized as in example 1, except that the NADH generator system (glucose and glucose dehydrogenase) was substituted with the sodium formate used at a concentration of 150 mM and formate dehydrogenase (amount: 9 units) system. In these conditions, 80 mg L-carnitine was synthesized in 15 hours from 590 mg of carnitine hydrochloride.

Formate dehydrogenase used in this experiment was prepared as follows, starting from *Torulopsis candida* GFP 206 deposited at the Fermentation Research Institute, Agency of Industrial Science and Technology of Japan MITI (Bikoken) under serial numbr 3645. This yeast strain was cultivated with methanol as carbon source in the conditions of example 4 of the French patent specification 75/24320 of July 30, 1975. The cells were collected by decantation and 40 ml of the settled portion were admixed with 6 ml of 0.1 M potassium phosphate buffer (pH 6.8) and 30 g of glass balls (diameter 0.5 mm) and crushed by stirring in a crusher (3 periods of 1 mn at a temperature lower than 10° C.). After centrifugation, the light phase was adjusted to an ammonium sulfate concentration of 350 g per liter. The precipitate was eliminated and the ammonium sulfate concentration of the light phase was brought to 500 g per liter. The resulting precipitate was collected and dialysed with a potassium phosphate buffer (50 mM) at pH 6.8. It constituted the preparation of formate dehydrogenase to be used in the synthesis of carnitine.

EXAMPLE 6

NADH regeneration was effected in this example by chemical means, sodium dithionate ($Na_2S_2O_4$) being the reducer. Synthesis was effected in the absence of oxygen since the dithionate oxidizes in air. The dithionate was injected as basic solution gradually as it was consumed since it decomposed in acidic or neutral medium. The reaction medium contained in a volume of 50 ml: 100 mM potassium phosphate buffer of pH 7.8, 10 mM sodium dithionate, 1 mM NAD and 0.5 ml carnitine dehydrogenase (as obtained in example 1). Nitrogen (20 ml/mn) was passed through the reactor. Dehydrocarnitine was injected as in example 1 and the 600 mM sodium dithionite solution (also containing 200 mM of di-potassium carbonate) was injected in the absence of air at a rate of 0.5 ml/h. The temperature was maintained at 25° C. and the pH at 7.8. After a 21 h operation, L-carnitine was collected by passage on ion exchange resin as described in example 1.

EXAMPLE 7

Example 1 was repeated (synthesis of L-carnitine) except that the glucose concentration was brought to 400 mM and 0.02% b.w. sodium azide ($NaN_3$) was added as antiseptic, the other conditions being as in example 1. 2.7 g of L-carnitine were obtained in 89 h 30, the yield being 95%.

EXAMPLE 8

Example 1 (synthesis of L-carnitine) was repeated in the same conditions, except that the concentration of the solution of dehydrocarnitine hydrochloride was 1 M, the neutralization agent being 4 N potassium hydroxide. 1.52 g of L-carnitine was obtained in 18 h 30, the yield being close to 100%.

What we claim is:

1. A process for producing L-carnitine, which comprises reacting 3-dehydrocarnitine or one of its salts, in aqueous medium, simultaneously with:
   (a) carnitine dehydrogenase,
   (b) a coenzyme which may be utilized by carnitine dehydrogenase for reducing dehydrocarnitine, and
   (c) a reducing agent for the coenzyme.

2. A process according to claim 1, wherein the coenzyme (b) is present in a catalytic amount effective to reduce 3-dehydrocarnitine to L-carnitine, catalyzed by carnitine dehydrogenase, and in the presence of a reducing agent to regenerate the coenzyme.

3. A process according to claim 1, wherein carnitine dehydrogenase is present in a catalytic amount effective to catalyze the reduction of 3-dehydrocarnitine to L-carnitine.

4. A process according to claim 1, wherein the coenzyme is nicotinamide adenine dinucleotide.

5. A process according to claim 1, wherein dehydrocarnitine is injected as a solution of pH lower than 2 in rate-limiting proportion.

6. A process according to claim 1, wherein carnitine dehydrogenase is produced by bacteria of the Pseudomonas genus.

7. A process according to claim 1, wherein carnitine dehydrogenase is produced by bacteria of the *Pseudomonas fluorescens* group.

8. A process according to claim 1, wherein the reducing agent for the coenzyme consists of a system with at least two elements:
   (a) a compound with an oxidizable group, a formate or molecular hydrogen, the element (a) being present at least in a stoichiometric amount with respect to 3-dehydrocarnitine, and
   (b) an enzyme suitable for the oxidation of element (a).

9. A process according to claim 8, wherein the reducing system for the coenzyme comprises:
   (a) glucose and
   (b) glucose dehydrogenase.

10. A process according to claim 8, wherein the reducing system for the coenzyme comprises:
    (a) a formate and
    (b) formate dehydrogenase.

11. A process according to claim 8, wherein the reducing system for the coenzyme comprises:
    (a) ethanol and
    (b) alcohol dehydrogenase.

12. A process according to claim 11, wherein the acetaldehyde formed by oxidation of ethanol is removed gradually as it is formed.

13. A process according to claim 11, wherein the reducing system further comprises aldehyde dehydrogenase.

14. A process according to claim 8, wherein the pH is from 6.5 to 8.5.

15. A process according to claim 8, wherein the enzyme (b) is used in the form of a microorganism containing said enzyme.

16. A process according to claim 8, wherein the enzyme (b) is immobilized on a solid carrier.

17. A process according to claim 1, wherein the reducing agent for the coenzyme onsists of an alkali metal dithionite.

18. A process according to claim 1, wherein the pH of the reaction is from 6.5 to 8.5.

19. A process according to claim 1, wherein the temperature of the reaction is from 20° to 45° C.

20. A process according to claim 1, wherein at least one of the enzymes used for the synthesis is in the form of a microorganism containing said enzyme.

21. A process according to claim 1, wherein at least one of the enzymes used for the synthesis is immobilized on a solid carrier.

22. A process according to claim 1, wherein the temperature in 10°–60° C. and the pH is from 5.5 to 10.

23. A process according to claim 1, which further comprises the steps of contacting the liquid reaction medium containing the resultant L-carnitine with an acidic cation exchange resin, eluting the resin with aqueous ammonia, and evaporating the solvent from the eluate fraction containing L-carnitine.

* * * * *